(12) United States Patent
Valen et al.

(10) Patent No.: US 10,980,617 B2
(45) Date of Patent: Apr. 20, 2021

(54) IMPLANTABLE SURGICAL SCREW FOR BONE RECONSTRUCTION

(71) Applicants: Maurice Valen, Jamaica, NY (US); Andrew W Valen, Hollis Hills, NY (US)

(72) Inventors: Maurice Valen, Jamaica, NY (US); Andrew W Valen, Hollis Hills, NY (US)

(*) Notice: Subject to any disclaimer, the term of this patent is extended or adjusted under 35 U.S.C. 154(b) by 0 days.

(21) Appl. No.: 15/050,225

(22) Filed: Feb. 22, 2016

(65) Prior Publication Data

US 2016/0242874 A1 Aug. 25, 2016

Related U.S. Application Data

(60) Provisional application No. 62/119,535, filed on Feb. 23, 2015.

(51) Int. Cl.
  *A61C 8/02* (2006.01)
  *A61C 8/00* (2006.01)
  *A61B 17/86* (2006.01)

(52) U.S. Cl.
  CPC ........ *A61C 8/0006* (2013.01); *A61B 17/8615* (2013.01); *A61C 8/0024* (2013.01); *A61C 8/0045* (2013.01)

(58) Field of Classification Search
  CPC ... A61C 8/0006; A61C 8/0024; A61C 8/0025; A61C 8/0045; A61C 8/0069; A61C 2008/0046
  USPC .................................................. 433/173, 174
  See application file for complete search history.

(56) References Cited

U.S. PATENT DOCUMENTS 4,185,383 A * 1/1980 Heimke .................. A61C 8/00
  433/173
4,560,353 A * 12/1985 Schulte ................ A61C 8/0019
  433/173
4,940,467 A * 7/1990 Tronzo ................. A61B 17/742
  606/304

(Continued)

OTHER PUBLICATIONS

Valen, Maurice, "The relationship between endosteal implant design and function: Maximum stress distribution with computer-formed three-dimensional Flexi-Cup blades", J. of Oral Implantol, 11, 49-71, 1983.

(Continued)

*Primary Examiner* — Yogesh P Patel
*Assistant Examiner* — Stephen R Sparks
(74) *Attorney, Agent, or Firm* — Maxine L. Barasch; Keohane & D'Alessandro, PLLC

(57) ABSTRACT

Aspects of the present invention include a screw device configured for implantation into human bone for dental and bone restoration purposes, or animal long bone. More particularly, embodiments of the present invention include a surgical screw having a surgical pinpoint tip, a head, a set of threads having a dynamic surgical region including quantified progressing minor diameters and a stabilizing surgical region including a substantially equal and parallel minor diameter between threads, and in some embodiments, an annular region and/or a tapered region. The set of threads are surgically sharp at the crest. The combination of these features enables the screw to be implanted without use of a drill or osteotome and without breaking.

6 Claims, 10 Drawing Sheets

(56) References Cited

U.S. PATENT DOCUMENTS

| | | | | |
|---|---|---|---|---|
| 5,061,181 A * | 10/1991 | Niznick | A61C 8/0022 433/174 |
| 5,199,873 A * | 4/1993 | Schulte | A61C 8/0018 433/173 |
| 5,300,076 A * | 4/1994 | Leriche | A61B 17/8635 411/395 |
| 5,527,183 A * | 6/1996 | O'Brien | A61C 8/0001 433/173 |
| 6,030,162 A * | 2/2000 | Huebner | A61B 17/1682 411/263 |
| 6,364,663 B1 * | 4/2002 | Dinkelacker | A61C 8/0018 433/173 |
| 6,511,481 B2 | 1/2003 | von Hoffmann | A61B 17/68 606/67 |
| 6,517,542 B1 * | 2/2003 | Papay | A61B 17/0401 606/232 |
| 6,585,740 B2 | 7/2003 | Schlapfer | A61B 17/863 411/380 |
| 6,887,243 B2 * | 5/2005 | Culbert | A61B 17/68 606/65 |
| 6,908,465 B2 | 6/2005 | von Hoffmann | A61B 17/68 606/67 |
| 6,951,561 B2 * | 10/2005 | Warren | A61B 17/68 606/328 |
| 7,033,398 B2 * | 4/2006 | Graham | A61B 17/562 606/304 |
| 7,857,832 B2 * | 12/2010 | Culbert | A61B 17/1637 606/246 |
| 8,197,511 B2 * | 6/2012 | Miller | A61B 17/0401 606/232 |
| 8,277,218 B2 * | 10/2012 | D'Alise | A61C 8/0025 433/174 |
| 8,668,725 B2 | 3/2014 | Smisson, III | A61B 17/863 606/286 |
| 9,452,028 B1 * | 9/2016 | Niznick | A61C 8/0022 |
| 9,522,028 B2 * | 12/2016 | Warren | A61B 17/8685 |
| 9,700,387 B2 * | 7/2017 | Sanchez | A61C 8/0006 |
| 9,855,117 B2 * | 1/2018 | Hwang | A61C 3/02 |
| 9,987,057 B2 * | 6/2018 | Lawson | A61B 17/8894 |
| 2004/0044345 A1 | 3/2004 | DeMoss | A61B 17/8625 606/916 |
| 2004/0049201 A1 * | 3/2004 | Dinkelacker | A61C 8/0018 606/86 R |
| 2004/0146834 A1 * | 7/2004 | Haessler | A61B 17/863 433/174 |
| 2005/0101961 A1 * | 5/2005 | Huebner | A61B 17/8605 606/304 |
| 2005/0137598 A1 * | 6/2005 | Auth | A61B 17/8635 606/281 |
| 2006/0110707 A1 * | 5/2006 | Perez Davidi | A61C 8/0024 433/173 |
| 2006/0149263 A1 * | 7/2006 | Newcomb | A61B 17/8625 606/311 |
| 2007/0083206 A1 * | 4/2007 | Du | A61B 17/8635 606/279 |
| 2008/0243192 A1 * | 10/2008 | Jacene | A61B 17/8047 606/290 |
| 2009/0305191 A1 * | 12/2009 | Jandali | A61C 8/0089 433/174 |
| 2010/0055645 A1 * | 3/2010 | Mullaly | A61C 8/0025 433/174 |
| 2011/0123951 A1 * | 5/2011 | Lomicka | A61C 8/0012 433/174 |
| 2011/0123953 A1 * | 5/2011 | Jorneus | A61C 8/0022 433/174 |
| 2011/0200969 A1 * | 8/2011 | Schroering | A61C 8/0018 433/174 |
| 2011/0313528 A1 * | 12/2011 | Laubert | A61F 2/4455 623/17.16 |
| 2012/0077151 A1 * | 3/2012 | Nary Filho | A61C 8/006 433/174 |
| 2012/0172658 A1 * | 7/2012 | Bjorn | H04R 25/606 600/25 |
| 2012/0265258 A1 * | 10/2012 | Garvey | A61B 17/8685 606/315 |
| 2013/0309632 A1 * | 11/2013 | Sanders | A61C 1/084 433/174 |
| 2015/0044638 A1 * | 2/2015 | Baez | A61C 8/0025 433/174 |
| 2015/0086942 A1 * | 3/2015 | Hwang | A61C 3/02 433/174 |
| 2016/0015483 A1 * | 1/2016 | Kumar | A61C 8/0012 606/301 |
| 2016/0166358 A1 * | 6/2016 | Thome | A61C 8/0075 433/174 |
| 2016/0166359 A1 * | 6/2016 | Flach | A61C 8/0022 433/174 |
| 2016/0242820 A1 * | 8/2016 | Whipple | A61B 17/8695 |

OTHER PUBLICATIONS

Valen, Maurice et al., "Establishment of an implant selection protocol for predetermined success. Journal of Oral Implantology", vol. XVI, No. 3 166-171, 1990.

Valen, Maurice et al., "Chapter 15—Flexi-Cup three dimensional blade implant device. Endosteal Dental Implants",174-187, 1991.

Valen, Maurice et al., "LaminOss® Immediate-Load Implants: Part I—Introducing Osteocompression in Dentistry. J Oral Implantol", 26(3)177-184, 2000.

* cited by examiner

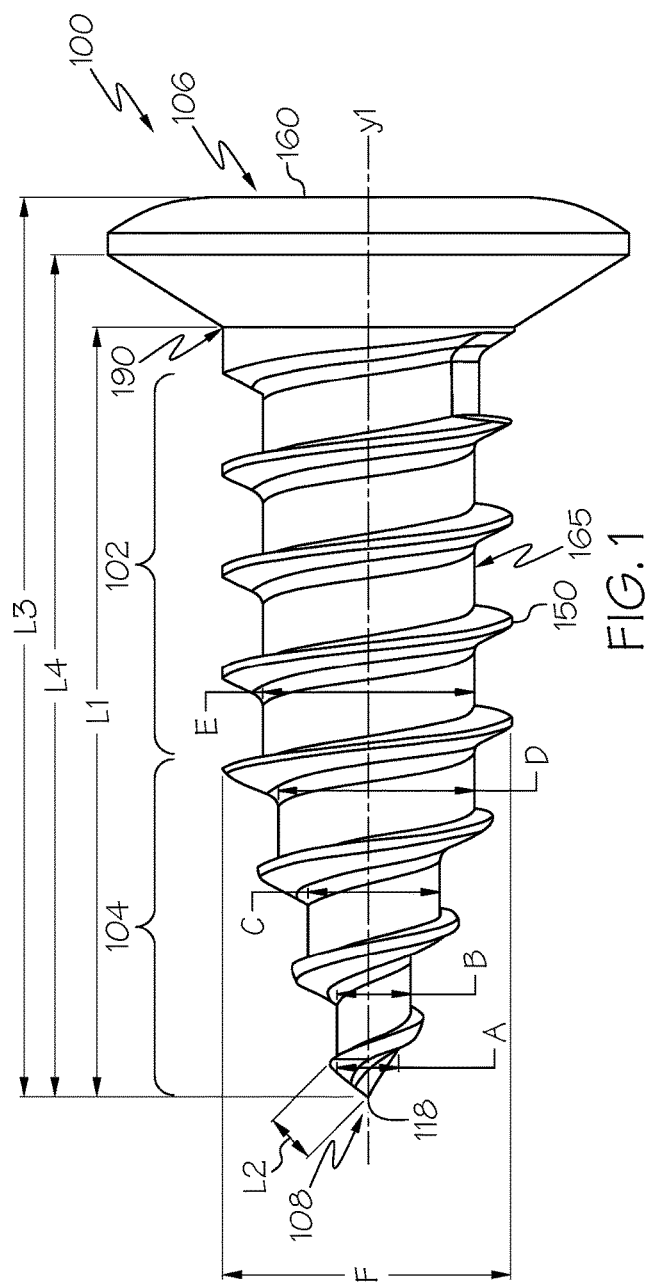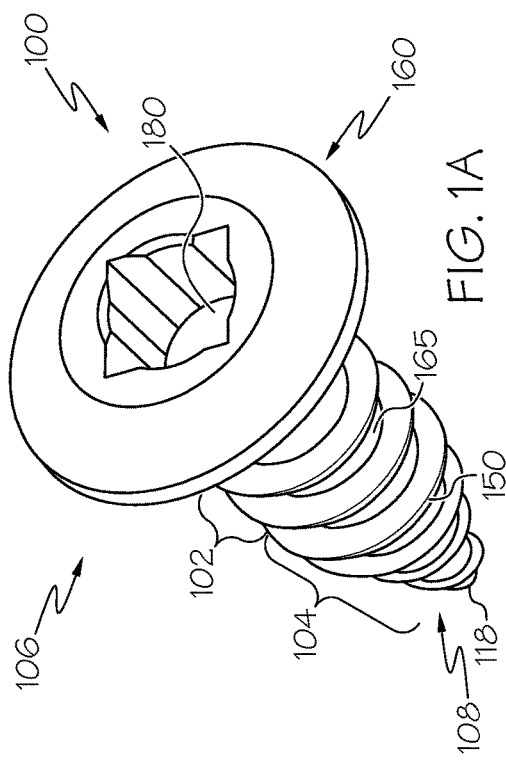

| STATIC COMPRESSIVE STRENGTH OF MAXILLARY CANCELLOUS BONE 10 MPa ||
|---|---|
| APPLIED FORCE (IN POUNDS) | REQUIRED IMPLANT LOAD BEARING AREA (LBA) |
| 1 | 0.444 |
| 5 | 2.220 |
| 10 | 4.450 |
| 15 | 6.670 |
| 20 | 8.900 |
| 25 | 11.120 |
| 30 | 13.350 |
| 35 | 15.570 |
| 40 | 17.790 |
| 45 | 20.020 |
| 50 | 22.240 |

FIG. 10

| STATIC COMPRESSIVE STRENGTH OF MANDIBULAR CANCELLOUS BONE 15 MPa ||
|---|---|
| APPLIED FORCE (IN POUNDS) | REQUIRED IMPLANT LOAD BEARING AREA (LBA) |
| 1 | 0.296 |
| 5 | 1.480 |
| 10 | 2.970 |
| 15 | 4.450 |
| 20 | 5.930 |
| 25 | 7.410 |
| 30 | 8.900 |
| 35 | 10.380 |
| 40 | 11.860 |
| 45 | 13.350 |
| 50 | 14.830 |

FIG. 11

IMPLANTABLE SURGICAL SCREW FOR BONE RECONSTRUCTION

CROSS-REFERENCE TO RELATED APPLICATION

The present patent document claims priority to U.S. provisional patent application Ser. No. 62/119,535, filed Feb. 23, 2015, titled "IMPROVED IMPLANTABLE SURGICAL SCREW FOR BONE RECONSTRUCTION", the disclosure of which is incorporated herein by reference.

FIELD OF THE INVENTION

Embodiments of the present invention are directed to an implantable screw for dental bone restoration purposes, and more particularly, a screw having a unique geometric configuration for improved ease of installation and lifespan for bone augmentation, among other benefits.

BACKGROUND

When a person loses one or more adult teeth, he/she is left with an empty space in his/her mouth where the one or more lost teeth were. Over time, many problems can occur from leaving this space untreated, such as bone loss, shifting of surrounding teeth, etc. Dental implants have been created/designed to replace lost teeth. Nevertheless, there are difficulties with conventional implants. In some cases, there may not be sufficient available bone areas for application of an implant. Many implants currently on the market require pre-drilled holes in the subject (e.g., osteotomy) prior to installation of an implant. Additionally, breaking/loss of an implant and bone necrosis during and after installation may occur. There exists a need for improvement in the field of bone augmentation for better implant predictability.

SUMMARY

Aspects of the present invention include a screw device configured for implantation into human maxillary and/or mandibular bone for dental and bone restoration purposes or in animals' long bones. More particularly, embodiments of the present invention include a surgical screw having a surgical pinpoint tip to start an osteotomy, a head, a dynamic surgical region having quantified progressing minor diameters to expand bone within physiologic limits of specific quantified measurements to function within biologic limits over a first set of threads, a stabilizing surgical region having substantially equal and parallel minor diameters compressing bone equidistantly between threads that provide helical fixation for the screw without backing out under function, and in some embodiments, an annular region and/or a tapered region to control migration of connective tissue by sealing bone dynamically with the annular region and/or tapered region for vertical screw adjustments dictated by bone quality at time of delivery. This combination of these features enables driving torque from the head of the screw through to the surgical pinpoint tip region, permitting the screw to be installed without breaking at any part of the screw body, and particularly without breaking near the head/neck junction.

In a first aspect, embodiments of the invention include a surgical screw, comprising: a shaft having a dynamic surgical region and a stabilizing surgical region; the shaft comprising a set of threads disposed thereon, wherein the set of threads extends from a pinpoint surgical cutting tip at a first end of the shaft through the dynamic surgical region and to the stabilizing surgical region; wherein the set of threads comprises a first set of minor diameters extending through the dynamic surgical region, the first set of minor diameters comprising four progressively increasing parallel minor diameters from the pinpoint surgical tip toward an interface of the dynamic surgical region with the stabilizing surgical region, and wherein the set of threads comprises a plurality of minor diameters of equal size extending from the interface toward a second end of the screw shaft.

In a second aspect, embodiments of the invention include a screw device comprising: a thread having a first set of minor diameters and a second set of minor diameters, wherein the first set of minor diameters comprises four progressively increasing parallel minor diameters, and wherein the second set of minor diameters comprises a plurality of minor and major diameters of equal size dimensions; wherein the first set of minor diameters are substantially parallel to one another; and wherein the first set of minor diameters comprises: a first minor diameter of approximately 0.25 mm, a second minor diameter of approximately 0.43 mm, a third minor diameter of approximately 0.79 mm, and a fourth minor diameter of 1.12 mm.

In a third aspect, embodiments of the present invention include a method of installing a screw device into bone of a patient without first drilling holes comprising: preparing an implant site for insertion of the screw device; providing a screw device, the screw device comprising: first set of minor diameters and a second set of minor diameters, wherein the first set of minor diameters comprises four progressively increasing parallel minor diameters, and wherein the second set of minor diameters comprising a plurality of minor diameters of equal size; aligning a surgical pinpoint tip of the screw device with a position on a bone at the implant site; and pushing the screw into the bone.

BRIEF DESCRIPTION OF THE DRAWINGS

These and other objects, features, and characteristics of the present invention will become more apparent to those skilled in the art from a study of the following detailed description in conjunction with the appended claims and drawings, all of which form a part of this specification. In the drawings:

FIG. 1 shows a side view of a fully-threaded screw having an approximately 5 millimeter (mm) length according to an embodiment of the present invention.

FIG. 1A shows an isometric view of the screw of FIG. 1.

FIG. 10 is a chart of static compressive strength of maxillary cancellous bone.

FIG. 11 is a chart of static compressive strength of mandibular cancellous bone.

Figure 2:
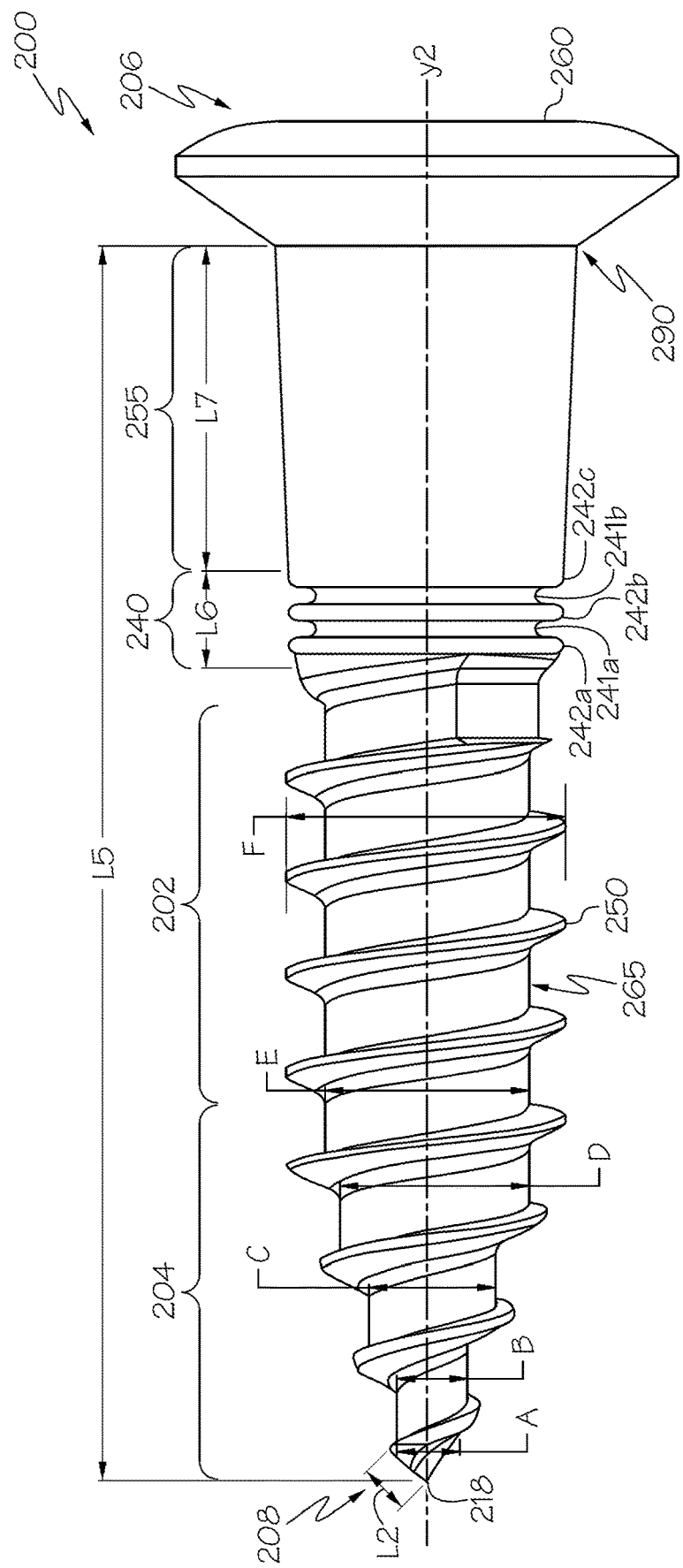
FIG. 2 shows a side view of a partially-threaded screw having an approximately 6-14 mm length with parallel annulars and a tapered region according to an embodiment of the present invention.

The drawings are not necessarily to scale. The drawings are merely schematic representations, not intended to portray specific parameters of the invention. The drawings are intended to depict only typical embodiments of the invention, and therefore should not be considered as limiting the scope of the invention. When used, like numbering represents like elements. In some cases, certain reference numbers may not be shown in some drawings for the sake of clarity.

DETAILED DESCRIPTION OF ILLUSTRATIVE EMBODIMENTS

The present invention will now be described fully hereinafter with reference to the accompanying drawings, in which preferred embodiments of the invention are shown. Like numbers refer to like elements of embodiments of the invention throughout. This invention may, however, be embodied in many different forms and should not be construed as limited to the embodiments set forth herein. Rather, these embodiments are provided so that this disclosure will be thorough and complete, and will fully convey the scope of the invention to those skilled in the art. Those of ordinary skill in the art will realize that the following embodiments of the present invention are only illustrative and are not intended to be limiting in any way. Other embodiments of the present invention will readily suggest themselves to such skilled persons having the benefit of this disclosure. In the description, details of well-known features and techniques may be omitted to avoid unnecessarily obscuring the presented embodiments.

The terminology used herein is for the purpose of describing particular embodiments only and is not intended to be limiting of this disclosure. As used herein, the singular forms "a", "an", and "the" are intended to include the plural forms as well, unless the context clearly indicates otherwise. Furthermore, the use of the terms "a", "an", etc., do not denote a limitation of quantity, but rather denote the presence of at least one of the referenced items. It will be further understood that the terms "comprises" and/or "comprising", or "includes" and/or "including", when used in this specification, specify the presence of stated features, region s, integers, steps, operations, elements, and/or components, but do not preclude the presence or addition of one or more other features, region s, integers, steps, operations, elements, components, and/or groups thereof.

Reference throughout this specification to "one embodiment," "an embodiment," "embodiments," "exemplary embodiments," "some embodiments," or similar language means that a particular feature, structure, or characteristic described in connection with the embodiment is included in at least one embodiment of the present invention. Thus, appearances of the phrases "in one embodiment," "in an embodiment," "in embodiments", "in some embodiments", and similar language throughout this specification may, but do not necessarily, all refer to the same embodiment. It will be understood that one skilled in the art may cross embodiments by "mixing and matching" one or more features of one embodiment with one or more features of another embodiment.

The terms "overlying" or "atop", "positioned on, "positioned atop", or "disposed on", "underlying", "beneath" or "below" mean that a first element, such as a first structure (e.g., a first layer) is present on a second element, such as a second structure (e.g. a second layer) wherein intervening elements, such as an interface structure (e.g. interface layer) may be present between the first element and the second element.

As used herein, the following terms are associated with the following meanings:

The "dynamic surgical region" refers to a surgical configuration feature that is typically substantially the same for all screw lengths of screws of embodiments of the present invention.

The "stabilizing surgical region" or "stabilizing region" (used interchangeably herein) refers to a region of the screw configured to stabilize the screw after installation in a patient's bone.

The "major diameter" refers to the largest knife-sharp helical diameters of a screw thread as measured at the crest of the thread.

The "minor diameter" refers to the smallest diameter of a screw thread as measured at the interface of the shaft of the body of the screw.

"Set" means "at least one".

Embodiments of the invention include a novel screw device (or "screw"). Embodiments of the screw devices of the present invention are configured for implantation into human maxillary and/or mandibular bone for dental and bone restoration purposes or animal's long bone. The screws of embodiments of the invention may be used for stabilization and fixation of bone grafts, bone blocks, bone filling materials, and/or barrier membranes used to regenerate bone in the oral cavity. The screw may be configured for, without limitation, receipt of loads during dental bone graft fixation procedures, and/or securing of (e.g., titanium) mesh, membranes, bone blocks, titanium plates, flexible bone strips, and other devices. For example, the screw may be configured for securing of bone grafting particulates in osseous defects where rigidity is required to avoid any movement of the grafted sites that will hinder healing and angiogenic activity prior to new bone formation. In some implementations, embodiments of the inventive screw are implantable into bone for medical uses in parts of a human or animal body other than the mandible or maxilla.

Embodiments provide a dental screw having a head, a non-tapered helix, and a graduated (i.e. having step-down parallel minor diameters) helix extending from the non-tapered helix to a pinpoint. More particularly, embodiments of the present invention include a surgical screw having a surgical pinpoint tip, a head, a quantified progressing minor diameter region over a set of threads noted as the dynamic surgical region, a stabilizing surgical region having a substantially equal and parallel minor diameter among knife-sharp helical threads, and in some embodiments, an annular region and/or a tapered region (without helical threads). The combination of these features results in superior driving torque from the head of the screw to the surgical sharp pinpoint tip region. This allows the screw to be installed with ease without breaking at any part of the screw body, and more particularly, without breaking near the head/neck junction, where most of the mechanical load is traditionally concentrated.

Embodiments of the screw of the present invention further include a screw device having a first end as a pinpoint surgical tip and a second end having a screw head. Embodiments of the screw of the present invention include a set of threads wrapped as a knife-sharp helix around a screw shaft. In some embodiments, the threads extend across the length of the screw shaft between the head and pinpoint tip. The threads and shaft are configured to define a first set of minor diameters which transition to a second set of minor diameters. In some embodiments, the screws are made of medical grade titanium alloy (ASTM F136).

The first set of minor diameters includes four progressively graduated minor diameters (FIG. 1, see reference letters A, B, C, and D), having a helical spiral cutting thread resulting in four rotations around the shaft of the screw—minor diameter. These four minor diameters are apparent in a 2-dimensional view of the screw as shown at FIGS. 1 and 2. The helix in between such diameter width progressively grows from the surgically sharp pinpoint tip. The four minor diameters progressively increase in diameter from the pinpoint surgical tip. The first set of minor diameters defines the "dynamic surgical region", progressively expanding the host bone within physiologic limits without bone necrosis.

The second set of minor diameters includes a plurality of parallel minor diameters of substantially equal size extending around the shaft of the screw. This portion of the set of (at least one) threads defines the "stabilizing surgical region". The stabilizing surgical region functions to stabilize the surgical screw in the host bone, upon installation therein, without unwinding under load or dynamic force, as commonly experienced with a fully tapered screw.

In other words, the screw of the present invention has a set of threads including four progressively increasing parallel minor diameters (from a surgically sharp pinpoint tip) as well as an additional set of minor diameters, which are all substantially parallel to each other in size. This configuration, allows the screw to be locked in a host bone without backing out. In comparison, unlike the screw of the present invention, a screw with threads only of a progressively tapering minor and major diameters (i.e., without a stabilizing region) will typically back out of a host bone because such a screw has a triangular working surface from the tip to the screw head.

The unique geometrical relationship among the four progressively increasing parallel minor diameters of the dynamic surgical region of embodiments of the screw of the present invention functions by flexing bone within physiologic progressing limits having viscoelastic properties by three dimensional bone fixation in $mm^3$ of bone expansion. This feature allows embodiments of the screw to surgically self-drill into a host bone with ease, e.g., up to approximately 15 Newton centimeters (Ncm) without breaking. The three dimensional screw device surgically progresses into the bone without physiologic compromise or necrosis of the bone due to the progressively increasing parallel minor diameters of the dynamic surgical region. These incrementally increasing parallel minor diameters cause this device to compress bone progressively within acceptable physiologic limits. No pre-drilled holes in the host bone are needed. In other words, the knife-sharp helix (set of threads) of the screw cuts the bone and the minor diameters expand bone "gently enough" within physiologic limits without causing damage. Cancellous bone is essentially a viscoelastic substrate compared to titanium metal, having elastic modulus 5 times greater than bone. These differences in elastic moduli need to be compensated for by configuration. The inventor has found the structural features of the screws of embodiments of the invention to provide such compensation as calculated by cadaveric mandibular studies (Valen 1983) noting that one pound of force against bone by titanium metal will require 0.444 $mm^2$ in the bone to be in equilibrium (worst case scenario). Case in point and by configuration, the compressive bone support areas of this screw are noted as the distance between the major diameter and the minor diameters of the present invention or 0.457 $mm^2$ for each thread (see FIGS. 10-11). The entire contents of the following articles are incorporated herein by reference:
1. Valen M: The relationship between endosteal implant design and function: Maximum stress distribution with computer-formed three-dimensional Flexi-Cup blades. Journal of Oral Implantology 11(1):49-71, 1983.
2. Valen M and Schulman A: Establishment of an implant selection protocol for predetermined success. Journal of Oral Implantology 26(3):166-171, 1990.

The additional larger minor diameters of the stabilizing surgical region are of equal distance to one another and have parallel walls (in a 2-dimensional view), and functions to stabilize the screw by keeping it from backing out due to the viscoelastic properties of bone.

Moreover, the threads of embodiments of the screw are helical, having a crest which is surgically sharp. The helical threads are configured to progressively cut into a host bone with ease from the tip to the interface of the shaft with the screw head delivery mechanism.

In contrast to known devices, the embodiments of the screw of the present invention do not require holes drilled into a patient's bone prior to installation. Embodiments of the screw act as their own "osteotome"—Accordingly, a separate drill is not needed. This is achieved by the dynamic surgical region of an embodiment of the screw device possessing unique and gradual parallel increasing minor diameters and the knife-sharp cutting edge of the set of threads. This causes the screw to penetrate and flex the bone, incrementally increasing features for bone compression within physiologic limits. This process and method using the dynamic surgical region will establish the screw device in the bone by utilizing the stabilizing surgical region of an embodiment to secure the device in equilibrium. This avoids the common problem of unwinding experienced by conventional screws under function or load because their major and minor diameters are tapered. This also avoids the two-step process of first drilling a hole and then inserting the screw. Also the screw fits more snuggly because it drilled a hole, which it creates, instead of being wedged into a pre-drilled one.

These unique geometric features of embodiments of the present invention provide a controlled horizontal support and equilibrium of metal to bone support areas in $mm^2$ in a compressive mode as calculated in FIGS. 10 and 11 to avoid bone necrosis by offering adequate physiologic consideration for the host bone given the differences in elastic moduli of titanium metal and mechanical properties of human bone in a compressive mode.

FIG. 1 shows a side view of an embodiment of a fully threaded screw 100 of the present invention. FIG. 1A shows an isometric view of the screw of FIG. 1. The screw 100 has a first end 108 and a second end 106. The screw shown has a pinpoint 118 at the first end 108, a head 160 at the second end 106, a shaft 165, and at least one thread 150 disposed on the shaft 165. The shaft 165 runs along the screw's long axis, denoted as "y1" on FIG. 1. In the example embodiment shown, the shaft has a length (L1) of approximately 4.0 millimeters (mm). The pinpoint tip has a length (L2) of approximately. 0.25 mm. The screw has an approximate total length (L3) of 5.3 mm from the pinpoint tip to the top of the head, while the length (L4) from the pinpoint tip to the outer edge of the head is approximately 5 mm. In some embodiments, the screw may also be other total lengths, for example, selected from about 3.0 mm to about 24.0 mm.

In some embodiments, the maximum minor diameter (E) of the threads of the screw shown in FIG. 1 is approximately 1.22 mm, and occurs in the portion of the threads in the surgical stabilization region 102. In this embodiment, the maximum major diameter (F) of the threads is approximately 1.67 mm. In some embodiments, the maximum minor diameter and maximum major diameter may be of other dimensions, for example depending on variables such as bone quality. Looking from the second end 106 of the screw, the minor diameter decreases, or "steps down", to approximately 1.12 mm, as the helix retreats/transitions from the stabilizing region 102 to the dynamic surgical region 104 for the first time, as shown at D The next step down in minor diameter is to approximately 0.79 mm, as shown at C, followed by a step down to approximately 0.43 mm, as shown at B, and followed by the final step down to 0.25 mm, as shown at A, before transitioning to the "knife-edge" ("scalpel-like-edge") surgical pinpoint tip as shown at 118 In some embodiments, the stepped-down minor diameters may be of other dimensions. The surgical pinpoint tip 118 may have a length (L2) of approximately 0.10 mm. Conversely, looking from the first end 108 of the screw knife-edge surgical pinpoint tip, as the thread helix rotates (e.g., clockwise) from the pinpoint tip (which can be envisioned as a minor diameter) 118, the minor diameter steps up to approximately 0.25 mm at A, then steps up to approximately 0.43 mm at B, then steps up to approximately 0.79 mm at C, then steps up to approximately 1.12 mm at D, and then finally steps up to approximately 1.22 mm at E in the stabilizing region 102. The dimensions of the minor diameters at A-D are typically substantially the same as described herein regardless of the screw length. These allow embodiments of the screw to act as their own "osteotome".

The stabilizing region 102 has threads of equal minor diameters (E), as well as equal major diameters (F) to help stabilize the screw after installation in a patient's bone. Although shown in FIG. 1 with a helix having 4 rotations, in some embodiments the stabilizing region 102 may have a helix with more rotations. Further, the distance between the major diameters and minor diameters of the dynamic surgical region 104 are generally the same as the distance between the major diameters and minor diameters of the stabilizing region 102. The difference between the major diameter and the minor diameter is typically 0.457 mm$^2$ as demonstrated in FIGS. 10 and 11 requiring metal-to-bone support to be in equilibrium. The pitch of the threads is typically 0.609 mm.

The configuration (and measurements, therefore) of the dynamic surgical region of the embodiment disclosed hereinabove may be used for any screw lengths (approximately 3.0 mm-24.0 mm), with some minor adjustment/variation allowed/enabled based on the requirements of a particular task (e.g., host bone density, location). The configuration of the stabilizing region may vary depending on the particular task; however, in a preferred embodiment, the set of threads in the stabilizing region are always of substantially equal minor diameter. For example, some embodiments of the screw may have a stabilizing region that is longer or shorter than other embodiments, or may have more or fewer threads than other embodiments. In various embodiments, the major diameter (F) of the threads of the stabilizing region may be selected from between approximately 1.5 and 2.5 mm. For instance, in a non-limiting example, of measurements for the threads of the stabilizing region may be a minor diameter (E) of approximately 1.22 mm and a major diameter (F) of approximately 1.67 mm, with a thread pitch of approximately 0.62 mm±0.001. These measurements for elements of the stabilizing region are examples only, and non-limiting. For example, in some embodiments, there are more threads rotations than the number shown in the figures. The measurements may vary depending on the use/application.

Figure 2A:
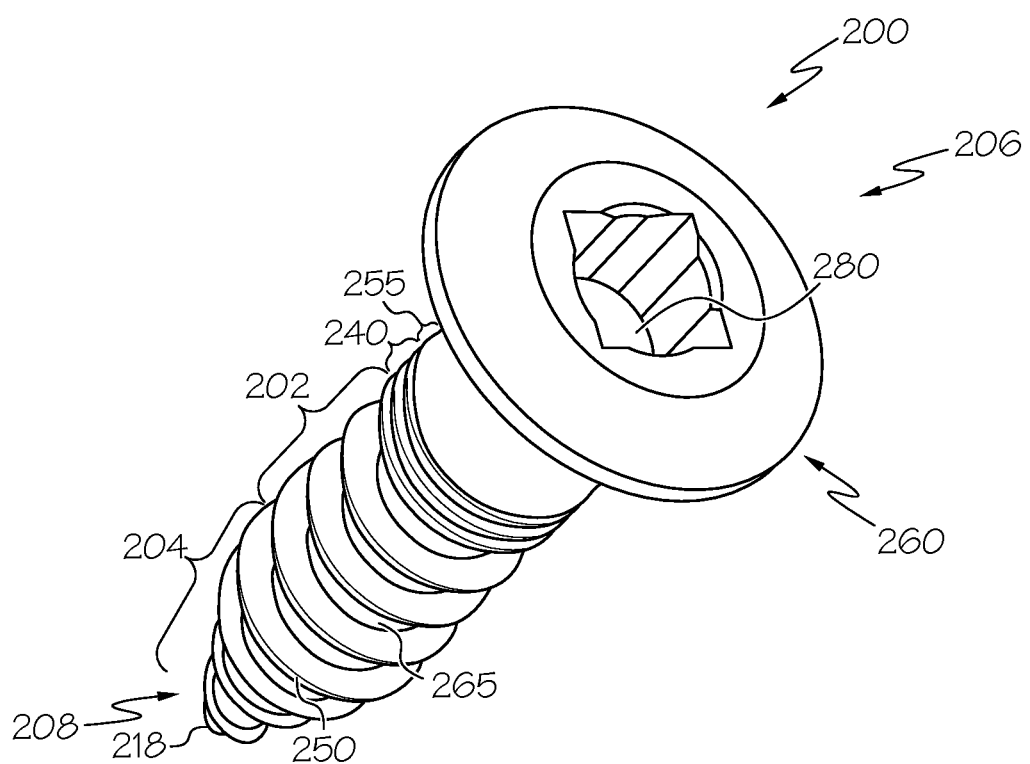
FIG. 2A shows an isometric view of FIG. 2.

FIG. 2 shows a side view of an embodiment of the screw 200, which is partially threaded, having an annular region 240 and a tapered region 255. FIG. 2A shows an isometric view of the screw of FIG. 2. The screw 200 has at a first end 208 with a pinpoint surgical osteotome tip 218 and a second end 206 with a screw head 260, as well as a dynamic surgical region 204 and stabilizing region 202. The screw shown has a minor diameter at A as a step up form pinpoint 218 at the first end 208, a head 260 at the second end 206, a shaft 265, and a set of (at least one) threads 250 disposed on the shaft 265. The major and minor diameters of the set of threads 250 (i.e. A-F) are substantially the same in measurements as denoted on FIG. 1 and described above. The angle and dimensions of the pinpoint 218 are the same as pinpoint 118 of FIG. 1.

Between tapered region 255 and the threaded shaft 265, in some embodiments, there may be annular region 240, having annulars 242a-c, for example, configured for a specified bone quality such as soft bone. These annulars slightly compress a host bone which moves into the designated annular concavities, e.g. 241a and 241b, and functions to lock the screw in place, for example, to prevent the screw potentially backing out in softer bone. This annular process prevents the downward migration and invagination of soft tissue (e.g., bone) by pressing the bone into the annular concavities due to bone compression within physiologic limits. The annulars, examples of which are shown at 242a, 242b, and 242c of the annular region 240, are parallel to one another and perpendicular to the screw's long axis, denoted as "y2" on FIG. 2.

Although only shown on the embodiment of FIGS. 2 and 2A, the embodiment of FIGS. 1 and 1A may, in some implementations, also include an annular region. Conversely, the screw of FIGS. 2 and 2A, in some implementations, may not include the annular region. In some embodiments, the annular region 240 may have one to eight annulars. In some embodiments, more than eight annulars may be included depending on the particular application. For example, in the embodiment of FIG. 2, three annulars 242a, 242b, and 242c are shown, creating two annular concavities 241a and 241b. As shown, in some non-limiting embodiments, the annulars may have the same diameter as the maximum major diameter of the threads.

In embodiments, the total length (L5) of screw 200 may vary between 6 mm and 24 mm. The length (L6) of the annular region may vary from approximately 0.5 mm to 3.0 mm. In some embodiments, the pitch of the annulars may be 0.2 mm, or other suitable measurement. In the example embodiment shown, the length (L6) of the annular region is approximately 0.6 mm, with the pitch of the annulars being 0.2. In some embodiments, the length of the tapered region (L7) is from approximately 1 mm to 8 mm. Note that these numbers are non-limiting examples, and the measurements and number of annulars may vary depending on the application.

Figure 3:
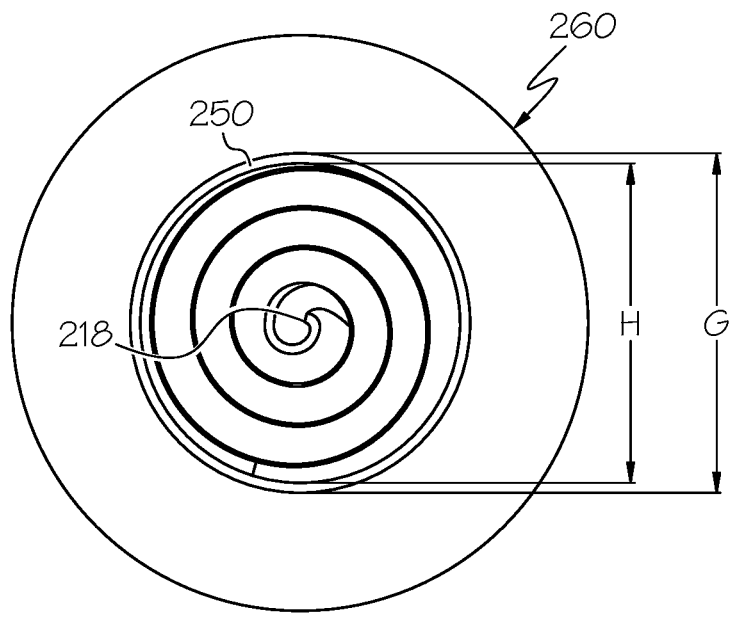
FIG. 3 shows a view of a first end of a screw of FIG. 2, having the pinpoint tip and a tapered feature with or without annulars according to an embodiment of the present invention.

Now referring to FIG. 3 in addition to FIG. 2, some embodiments of the screw may have a tapered region 255. FIG. 3 shows a top down view from the first end 208 of the screw of FIG. 2. The diameter of the tapered region 255 decreases towards the first end from a smooth interface with the screw head at an angle. For example, if the length of the tapered region 255 is 1.0 mm, the angle is 5.8 degrees from y2. If the length of the tapered region 255 is 8.0 mm, the angle is 0.73 degrees from y2. For example, in some embodiments the angle may be 14.5 degrees (from the longitudinal axis (y2 or y1) of the screw) to its interface with the stabilizing surgical region. The tapered region 255 typically has a substantially smooth surface to enable the clinician to move the screw from 1 mm to 3 mm by compressing the screw against the bone and feeling the resistance of bone quality by experience (or using a surgical dental motor set at 15 Ncm). In a non-limiting embodiment, the maximum minor diameter (G) of the tapered region 255, shown in the example of FIG. 2 and FIG. 3, may be approximately 1.78 mm, while the minimum minor diameter (H) may be approximately 1.67 mm. In embodiments, the tapered region 255 may have a length (L7) (see FIG. 2) of approximately 1.0 mm to 8.0 mm.

Figure 4:
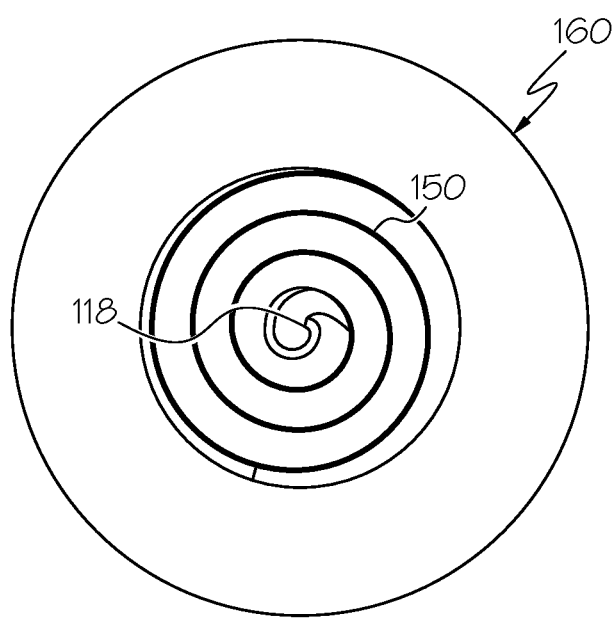
FIG. 4 shows a view of a first end of a screw of FIG. 1, having a surgical pinpoint tip and without a tapered region according to an embodiment of the present invention.

Referring now to FIG. 4, there is shown a view from the first end 108 from pinpoint surgical osteotome tip 118 of the screw of FIG. 1 without a tapered region as described with respect to FIGS. 2 and 3. As opposed to the view from the first end 208 shown in FIG. 3 of the screw of FIG. 2, the view shown in FIG. 4 of the screw of FIG. 1 does not have a tapered region. Rather, shaft 165 directly interfaces with screw head 160. FIG. 4 shows the pinpoint tip 118 and screw head 160. In this embodiment, the set of threads 150 extends from pinpoint tip 118 to screw head 160.

Figure 5:
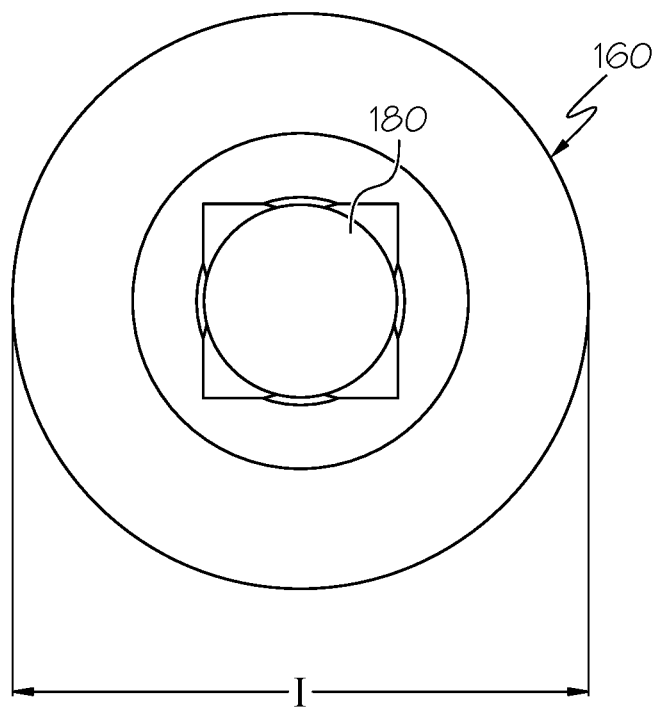
FIG. 5 shows a view from a second end of the screw of FIG. 1 having a screw head, showing a receptor site of the screw head according to an embodiment of the present invention.
Figure 6:
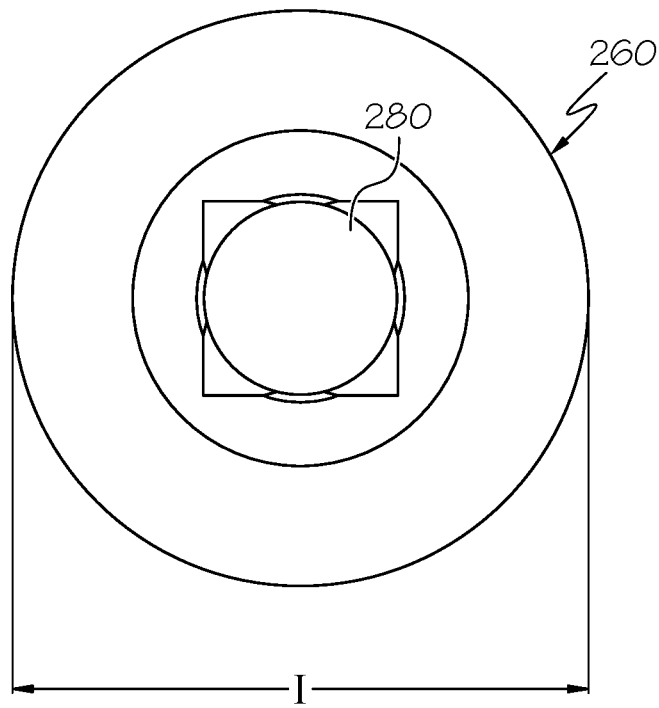
FIG. 6 shows a view from a second end of the screw of FIG. 2 having a screw head, showing a receptor site of the screw head according to an embodiment of the present invention.

Referring now to FIGS. 5 and 6, there is shown a top-down view of the screw head 160 and 260 of FIGS. 1 and 2 from the second end 106 or 206, respectively. The configuration of the screw head as shown may be substantially the same for any embodiment of the screw and for any screw shaft lengths herein described. The screw head of an embodiment of the present invention comprises features as described below. Typically, prior to use, the head of the screw may rest in a surgical cassette for ease of engagement and delivery. The head may have a diameter (I) of approximately 3 mm. In some embodiments, diameter (I) can range from 2.0 mm to 4.0 mm. For example, the diameter of the screw head (I) may be 3 mm.

The head 160 or 260 comprises a tapered head receptor site 180 or 280, respectively, for a "male" driver to engage with to pick up and deliver the screw. In some non-limiting embodiments, the head receptor site is configured for accepting a screw driver in the shape of a Morse taper. As shown, the receptor site may have a round taper with square broached corners. Other shaped receptor sites are possible in embodiments. In practice, a user may insert a, e.g., square tapered, screwdriver (not shown) into the square tapered receptor site 180 or 280, and uniaxially rotate, e.g., approximately 22° to 45° left or right, until the screw head has engaged with the driver. Typically, this may be indicated by a click heard or felt. The user may then press down on the driver to pick up the screw from the cassette and to deliver the screw to the surgical site by turning the driver in a clockwise direction. To disengage the screwdriver from the screw, the user typically may tilt the screwdriver left or right to loosen and release the connection between the driver and the screw.

Figure 12:
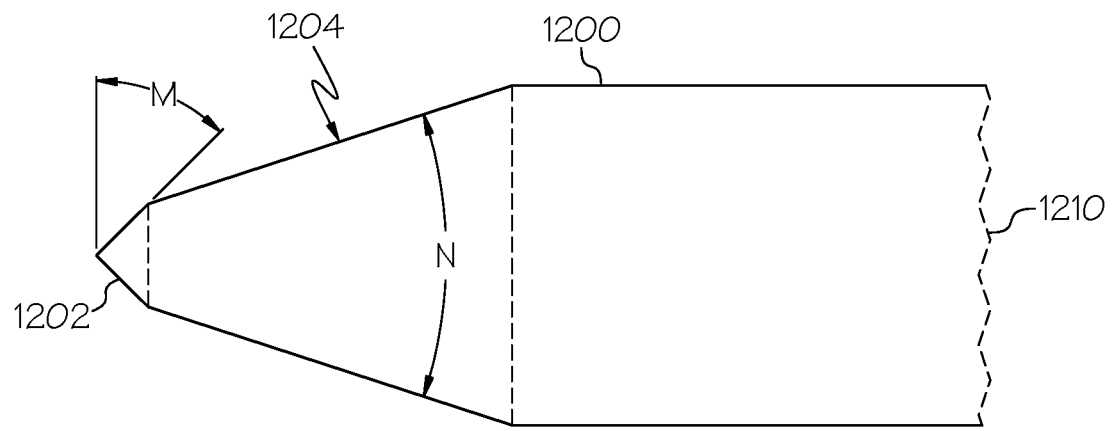
FIG. 12 shows a simplified schematic partial representation of a major diameter of the screw threads of the embodiments shown in FIG. 1 or FIG. 2.

Referring now to FIG. 12, there is shown a simplified schematic partial (i.e. cut away) representation of a major diameter of the screw threads of embodiments shown in FIG. 1 or FIG. 2. Note break line 1210 represents an "imaginary" break where the shaft and other elements would continue except for this being a partial diagram. As shown, 1200 represents the major diameter of the threads in either of the stabilizing or dynamic surgical region. Angle M represents the angle of a thread pinpoint tip 1202, which in some embodiments may be between approximately 39 degrees and 45 degrees. Angle N represents the angle of the major diameter of the threads in the dynamic surgical region 1204, which is 37 degree in all embodiments.

Figure 13:
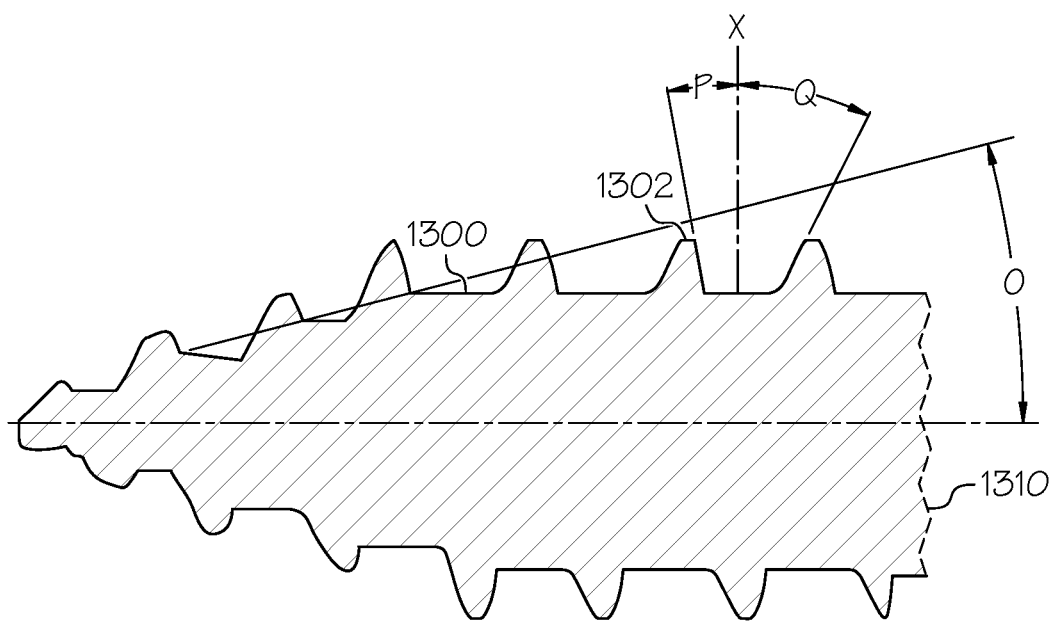
FIG. 13 is a simplified cross-sectional schematic of the shaft 1300, which represents a shaft of the embodiments of the screw in FIG. 1 or FIG. 2.

Referring now to FIG. 13, there is shown a simplified cross-sectional schematic of a shaft 1300, which represents the shaft 165 or 265 of the embodiments of the screw in FIG. 1 or FIG. 2. Note break line 1310 represents an "imaginary" break where the shaft and other elements would continue except for this being a partial diagram. Angle O shows the angle of the minor diameters in the dynamic surgical region, which in some embodiments is approximately 14.5 degrees. X represents the x-axis perpendicular to the screw's long axis, denoted as "y1" or "y2" in FIG. 1 or FIG. 2, respectively. Angles P and Q represent angles of each side of threads 1302 relating thereto, which in some embodiments comprise approximately 10 degrees and approximately 25 degrees, respectively.

In some embodiments, the screws may be manufactured using a Ti-6Al+4V alloy (ASTM F-136) and may adhere to standards tested under ASTM F-543. Manufacturing of a screw may be performed by a CNC Swiss Screw Machine (Haas Automation, Oxnard Calif.). In some manufacturing techniques, a titanium bar, usually 6 feet to 12 feet long, may be fed into the machine horizontally through an axis of the machine. When the bar is fed through incrementally, each screw may be cut by a predetermined software program (CNC) starting from the helix to the head and may be cut off after the head. The screws may then be gathered, deburred, and cleaned. Each screw may be placed in a die for holding concentrically. A hole may be drilled in the head uniaxially, followed by broaching of the corners to structure a square receptor site for a driver.

In summary, embodiments of the present invention include a screw with a surgical pinpoint tip osteotome, a head, a quantified progressing minor diameter region over a dynamic surgical region, a stabilizing region having threads of a substantially equal minor diameter, and in some embodiments, an annular region and/or a tapered region. In combination, these features results in excellent driving torque up to approximately 15 Ncm from the head of the screw to the surgical pinpoint tip region without breaking at any part of the screw body, and, particularly, without breaking near the head/neck junction area (190 of FIG. 1 and 290 of FIG. 2) of the screw shaft where most of the mechanical load is typically concentrated. Regardless of the screw length, the dynamic surgical region is substantially the same across different embodiments with a preferable maximum major diameter of approximately 1.67 mm, but the maximum major diameter could be less and/or vary depending on bone density of a patient.

Referring now to Table 2 of FIG. 7 and Tables 1 and 3 below, a set of yield strength and torque tests were performed on embodiments of screws of the present invention (hereinafter "Screw 1") having an overall length of 4.3 mm (without tapered region 255 or annular region 240), as well as on 4.0 mm length screws (hereinafter "Screw 2") having a similar length and width, which are a prototype manufactured by Impladent Ltd, tested at the University of Texas and which represent the current state of the art. Screw 2 lacks the features of the present invention. Both Screw 1 and Screw 2 are made of medical grade titanium alloy (ASTM F-136 Ti6Al+4V.

Table 1 below details the specifications of Screw 1, which is one embodiment of the present invention, and the specifications of Screw 2, the prototype manufactured by Impladent Ltd. experimentally representing the state of the art. Screws with a shaft length of approximately 4 mm were selected as the "worst case" device based on results of previous testing on small (3 mm, 4 mm, 5 mm), medium (6 mm, 8 mm) and long (10 mm, 12 mm, 14 mm) screw embodiments of the present invention. The 4 mm screws, in accordance with embodiments of the present invention, had the lowest average maximum torque value as determined by such previous testing; therefore, the 4 mm screw was identified as the "worst case" device manufactured from the same titanium alloy.

TABLE 1

Screw Comparisons

| Description | Screw 1 | Screw 2 |
|---|---|---|
| Square depth | .81 mm | .81 mm |
| Pilot hole depth | .94 mm | .94 mm |
| Head diameter | 3.0 mm | 2.5 mm |
| Overall length (including head) | 4.3 mm | 4.0 mm |
| Maximum Major diameter | 1.67 mm | 1.57 mm |
| Maximum Minor diameter | 1.22 mm | 1.09 mm |
| Head ring width | .13 mm | .15 mm |
| Thread Taper | 14.5° (in the Dynamic Surgical Region) | 19.0° |
| Size (fully threaded) | 4 mm | 4 mm |
| Grip length | 2.36 mm | 0.72 mm |
| Gauge length | 1.22 mm | 1.50 mm |
| Material | Ti6Al + 4V | Ti6Al + 4V |
| Test sample size | 5 screws | 5 screws |

A series of tests were performed on Screw 1 and Screw 2. More specifically, Screw 1 and 2 were subjected to: an Insertion Test to determine the torque required to insert each screw (insertion torque) into a test block; a Breaking Test to determine the breaking torque (maximum torque) and yield strength of the screws; and a Pullout Test to determine the force required to remove the screws from the test block. The results of these tests are shown in Table 2 of FIG. 7 and Table 3 below.

The insertion torques recorded for the Screws 1 and 2 are summarized in Table 3 below. In the Insertion Test, the screws were inserted in a 30 pounds per cubic foot (PCF) sawbone block at a torsional rate of 3 revolutions per minute (rpm). The torsional torque was recorded throughout the test, and the maximum insertion torque recorded during the test was considered the insertion torque. The screws were inserted until one thread was left exposed, at about 60% insertion. This was done to leave enough room to perform the Pullout Test, described further below. As can be seen in Table 3 below, Screw 1 of the present invention required a lower insertion torque and had a smaller variation than Screw 2.

TABLE 3

| | Tests | | | |
|---|---|---|---|---|
| | Max Torque (N · m) | Insertion Torque (N · m) | Safety Factor | Pullout Force (kN) |
| Screw 1 | 0.138 ± 0.078 | 0.006 ± 0.004 | 23 | 0.038 ± 0.012 |
| Screw 2 | 0.075 ± 0.017 | 0.008 ± 0.006 | 7.25 | 0.020 ± 0.005 |

Figure 7:
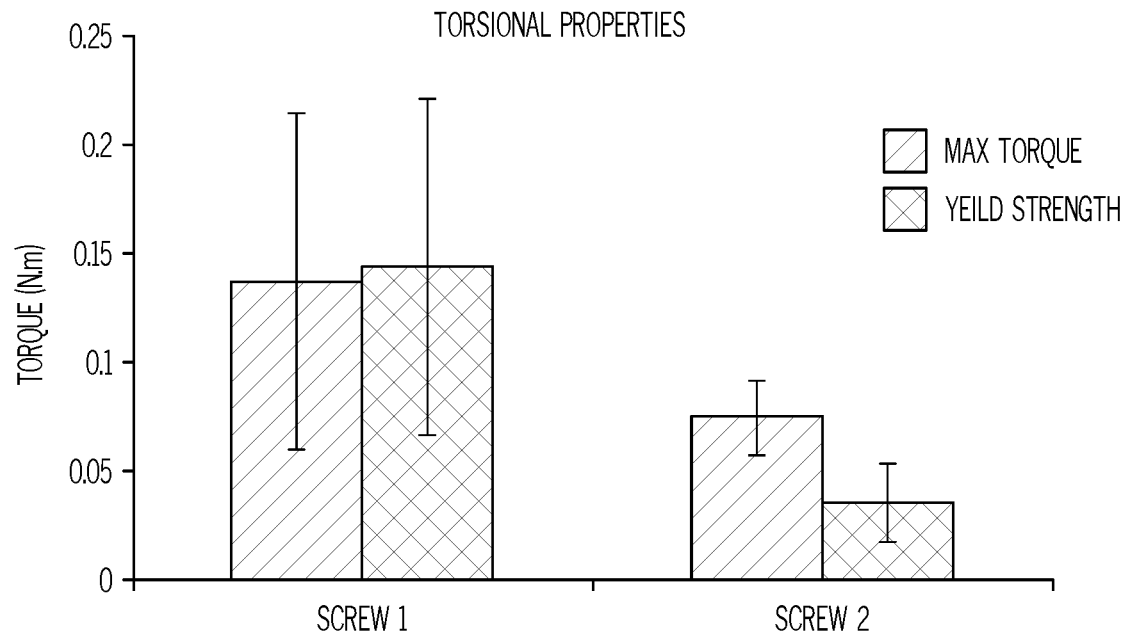
FIG. 7 shows maximum torque and yield strength for a screw according to an embodiment of the present invention.

The maximum torque and yield strength of Screw 1 and Screw 2 determined during the Breaking Test are shown in Table 2 of FIG. 7. The Yield Strength of each of Screw 1 and Screw 2 was calculated by the 2° offset method described in ASTM standard F543. As shown in FIG. 7, Screw 1 performed 3.8 times better as to Yield Strength and 1.8 times better as to Max Torque as compared to Screw 2. As visualized by FIG. 7, these values indicate almost a two times improvement (i.e., a 100% improvement) in Maximum Torque of Screw 1 as compared to Screw 2, and approximately a four times improvement for yield strength over Screw 2. The maximum torque values from the Breaking Test (the terms "Breaking Test" and "Yield Test" are used interchangeably herein) are further shown in Table 3 above. During testing, none of the Screw 1 devices of the present invention broke, as compared to Screw 2 that did break. As determined from previous trial tests, an aluminum test block fixed with pilot holes of depths that would allow one thread to be exposed, as per the ASTM F-136, was used in the Breaking Test. The pilot holes enabled the manual insertion of the self-drilling screws, which were stopped at the bottom of the hole. By using this method, the testers were able to restrict screw movement during the test. While both screws are marketed as 4 mm and fully threaded, slight design differences caused necessary deviations in the test setup for grip length and gage length, as shown above in Table 1. For example, Screw 2 of the current state of the art is 4 mm in length including the head, while screw 1 is 4.3 mm in length, including the head. The ASTM standard was followed in both instances to leave only one thread exposed. The rotation rate was set at 3 rpm for the test in order to standardize the test. The axial force required to hold the driver in the screw head and prevent any slippage was recorded for every test and is shown in Table 3 as the maximum torque (failure torque).

Table 3 also shows the relative safety factors that were calculated using the maximum forces from the Breaking Test. The safety factor is defined as the ratio of failure torque (maximum torque) to insertion torque. As shown above, Screw 1 demonstrated a safety factor of 23, which is more than a three time improvement on the 7.25 safety factor of Screw 2.

In a final test, the pullout force was determined in the Pullout Test. The screws inserted in the block, as described in the Insertion Test above, were subjected to an axial pullout load applied at a rate of 5 mm/min. The axial force and displacement were recorded throughout the test noting the maximum load and mode of failure (snap at neck of screw). The Pullout Test results are listed in Table 3 above, and show that the force required to remove Screw 1 was almost twice the force required to remove Screw 2.

Embodiments of the present invention can be used for any of a multitude of applications. As such applications of a surgical screw are generally known in the art, the following applications will only be discussed in brief and are not intended to be limiting. Non-limiting examples include the following:

Securing and splinting maxillary or mandibular bone fractures with various thicknesses of titanium mesh and plate devices in.

Growing vertical bone height and width using titanium mesh devices using bone grafts with or without dental implant devices to restore fractures.

Securing various types of organic and inorganic membranes, such as to bovine collagen membranes, PTFE plastic devices, human membranes, allografts and alloplasts and combinations thereof.

Securing flexible forms of synthetic block devices and monolithic human bone blocks. In such an instance, the advantage of an unthreaded portion of the screw, as demonstrated in some embodiments, does not bind to the bone block, and as a result, the screw helix does not pull the block away from the host bone because it is tapered and smooth in a sheering mode.

Using with membranes in dental tenting procedures as adjustable Tenting Screws. In this instance, the threaded portion of the screw of an embodiment engages with the host bone while the unthreaded portion of the screw head remains outside of the bone and functions as support for a membrane draped over the screw head creating a tenting effect. The area under the tent is filled with bone grafting material. The tapered features of the unthreaded portion allows the clinician to adjust the height of the screw in the osteotomy because the bone is viscoelastic within limits from 1-3 mm without compromising the bone and/or causing bone necrosis while the annular portion locks into the bone preventing any movement.

Figure 8:
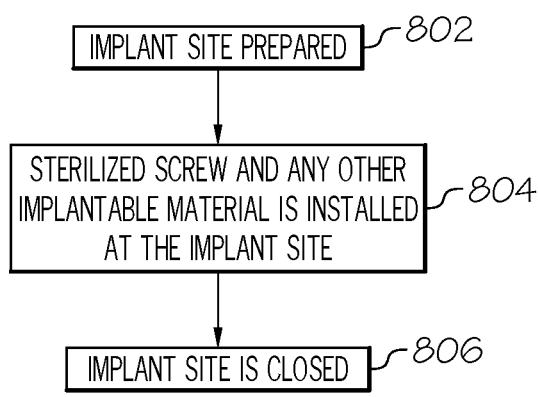
FIG. 8 shows a flow chart of surgical steps in accordance with some embodiments of the invention.

FIG. 8 shows, in summary, a method of use of the inventive screw. The implant site in the patient is prepared at 802. A sterilized screw and any other material to be implanted (such as mesh or bone graft) is installed at the prepared implant site, at 804. This may include aligning the pinpoint of the screw with the desired position of implanting, and turning the screw (with a driver, by hand, or another suitable mechanism) to push it into the bone. The gum or other tissue is sutured, closed, or otherwise finished, at 806. Note that more or fewer steps may be included. For example, the following is an example method of using embodiments of the screw of the present invention.

Removal of screw from cartridge:
A. Gently introduce a driver handle with the drive directly over the screw (uniaxially) and rotate 22°-45° left or right until a slight click is heard or felt indicating the screw has engaged with the driver. Press down firmly to pick-up the screw and deliver it to the surgical site.
B. To disengage the screwdriver from the screw tilt the screwdriver left or right to loosen and release the connection between the driver and screw.
C. For use with bone blocks, use 2.0 mm drill to make a hole through the bone block.
D. To preserve the surface, the titanium devices should be handled with clean instruments dedicated to titanium, or talc-free gloved hand.

Titanium Mesh with Bone Augmentation Protocol:
A. Titanium Mesh preparation (product supplied non-sterile):
 a. Take alginate of the jaw, identify the defect area and pour cast model.
 b. Overfill defect area by 15% with wax on the cast model (this is to provide a margin of safety when returning the pre-formed titanium mesh to the host after step (g) below).
 c. Place dental foil over wax.
 d. Cut white cardboard template to the desired bone restoration area on the model. Ensure adequate space to secure the mesh beyond the defect (3-5 mm).
 e. Place white cardboard template on top of the mesh and cut to size.
 f. Place titanium mesh on the cast model at the margin of the defect to establish a ridge and crease to create the desired buccal and lingual portions of the crest.
 g. Sterilize titanium mesh for clinical use inside the cassette (or with a sterilization bag) paying careful attention not to disturb the newly formed shape of mesh.
B. Surgery:
 a. Develop a full thickness flap with buccal vertical incisions releasing bilaterally one tooth beyond surgical site.
 b. Debride and decorticate surgical site with #4 round bur.
 c. Make holes through cortex to the endosteum with a 2.0 mm bur to maintain angiogenesis for at least 4 months during healing.
 d. Using Blood Syringe with large stainless steel orifice, collect blood to mix with bone graft in equal parts (1 ML blood per 1 cc bone graft). OsteoGen® (K843398, K881662, K923310, K033098) is the preferred graft for this procedure. Follow the instructions for use included with the surgeon's bone grafting material of choice.
 e. Control profuse bleeding with surgical gauze or hemostatic agent to avoid migration of bone augmentation material.
 f. Secure mesh lingually or buccally with one or two screws of embodiments of the present invention.
 g. Place bone graft mixture onto defect site of bone and against titanium of the screw to fill a defect.
 h. Place mesh into final positioning and secure with two more self-drilling screws of embodiments of the present invention.
 i. Underscore periosteal flap to separate tissue from bone and attain primary closure.
 j. Membrane is required if primary closure is not available.

Figure 9A:
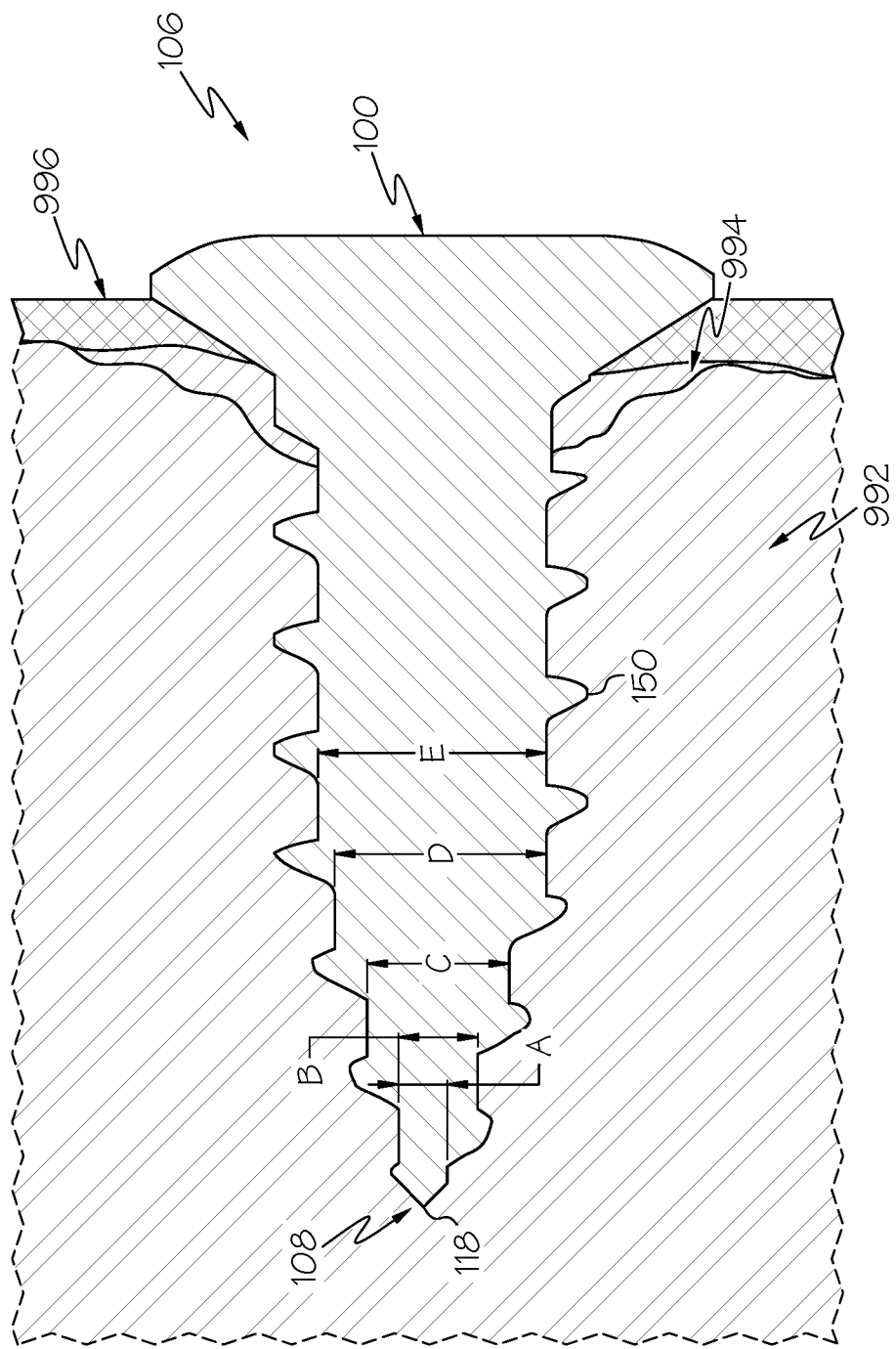
FIG. 9A shows a simplified illustration of an example of the screw 100 according to an embodiment of the present invention securing a bone graft and titanium mesh in a vertical defect in bone of a patient.
Figure 9B:
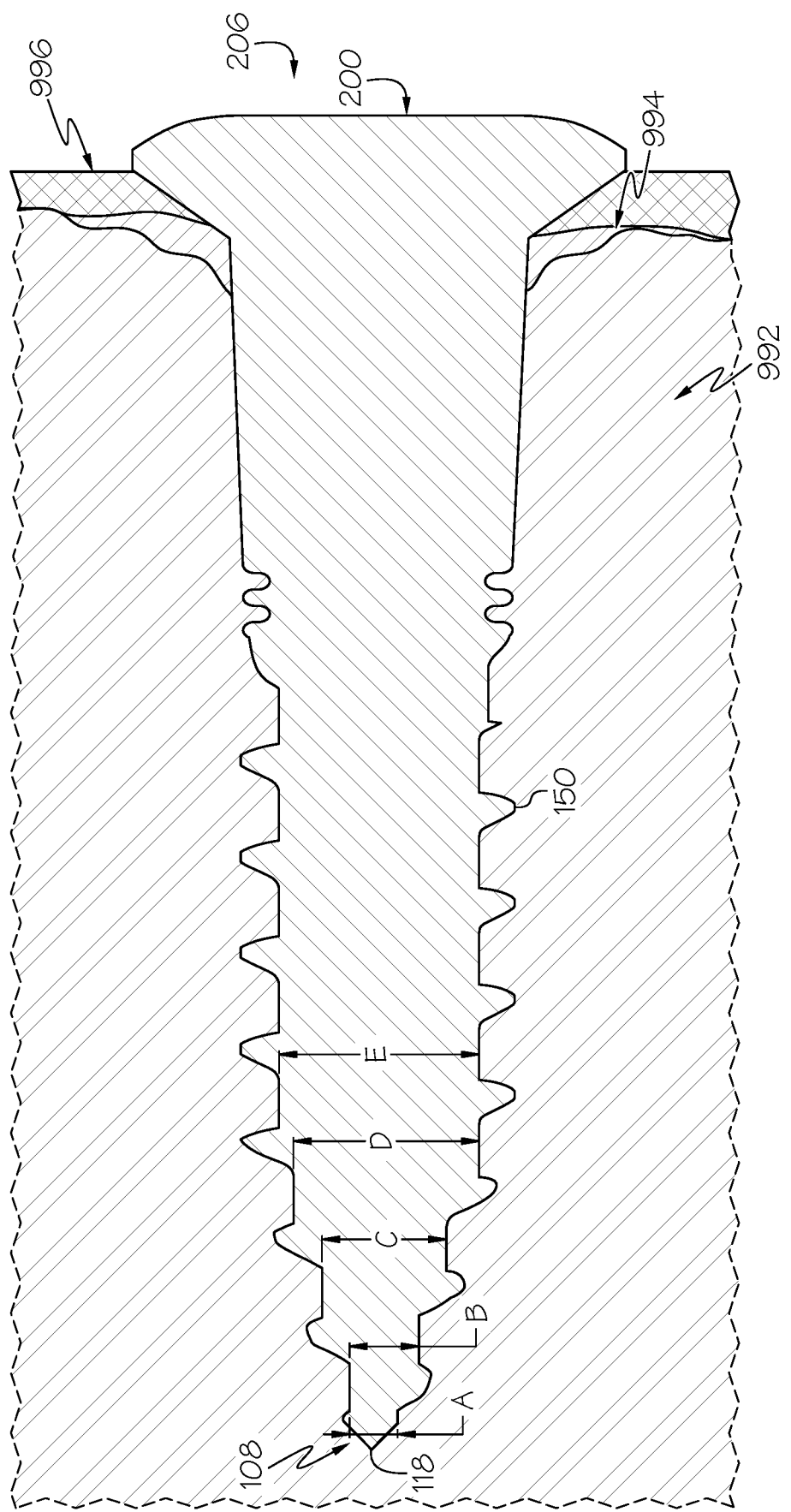
FIG. 9B shows a simplified illustration of an example of the screw 200 according to an embodiment of the present invention securing a bone graft and titanium mesh in a vertical defect in bone of a patient.

FIGS. 9A and 9B show a simplified cross-section of a screw 100 (in accordance with the embodiment of FIG. 1) and screw 200 (in accordance with the embodiment of FIG. 2), respectively, installed in bone 992 of a patient. Screw 100 holds bone graft 994 and mesh 996. This is an example of use of the screw in accordance with embodiments of the invention. Other uses and implementations are possible within the scope and spirit of the invention. In contrast to known devices, the embodiments of the screw of the present invention do not require holes drilled into a patient's bone prior to installation. This is achieved by the dynamic surgical region of an embodiment of the screw device possessing unique and gradual parallel increasing minor diameters and the knife-sharp cutting edge of the set of threads. This causes the screw to penetrate and flex the bone, incrementally increasing features for bone compression within physiologic limits. This process and method using the dynamic surgical region will establish the screw device in the bone by utilizing the stabilizing surgical region of an embodiment to secure the device in equilibrium. This avoids the common problem of unwinding experienced by conventional screws under function or load because their major and minor diameters are tapered. This also avoids the two-step process of first drilling a hole and then inserting the screw. Also the screw fits more snuggly because it drilled its own hole instead of being wedged into a pre-drilled one. It is apparent that there has been provided approaches for an implantable surgical screw and methods of use thereof.

Although the invention has been shown and described with respect to a certain preferred embodiment or embodiments, certain equivalent alterations and modifications will occur to others skilled in the art upon the reading and understanding of this specification and the annexed drawings. In particular regard to the various functions performed by the above-described components (assemblies, devices, circuits, etc.), the terms (including a reference to a "means") used to describe such components are intended to correspond, unless otherwise indicated, to any component which performs the specified function of the described component (i.e., that is functionally equivalent), even though not structurally equivalent to the disclosed structure which performs the function in the herein illustrated exemplary embodiments of the invention. In addition, while a particular feature of the invention may have been disclosed with respect to only one of several embodiments, such feature may be combined with one or more features of the other embodiments as may be desired and advantageous for any given or particular application. The flow diagrams depicted herein are provided by way of example. There may be variations to these diagrams or the steps (or operations) described herein without departing from the spirit of the invention. For instance, in certain cases, the steps may be performed in differing order, or steps may be added, deleted, or modified. All of these variations are considered a part of the present invention as recited in the appended claims.

We claim:

1. An adjustable, self-drilling, tenting screw, comprising:
a screw head comprising a screw-driver acceptor site therein;
a tapered region that interfaces with the screw head,
wherein the tapered region has a first end and a second end,
wherein the first end comprises a minimum diameter of the tapered region,
wherein a minimum diameter of the tapered region interfaces with an annular of a plurality of annulars, wherein each annular of the plurality of annulars are parallel to one another,
wherein the second end comprises a maximum diameter of the tapered region, and
wherein the second end interfaces with an underside of the screw head;
a shaft having a dynamic surgical region and a stabilizing surgical region, the shaft comprising a set of threads disposed thereon;
an annular region comprising the plurality of annulars, wherein each of the annulars of the plurality are separated by an annular concavity, and wherein each annular of the plurality has a diameter equal to a maximum major diameter of the set of threads;
wherein a first end of the annular region interfaces with the stabilizing surgical region;
wherein a second end of the annular region interfaces with the first end of the tapered region;
wherein the set of threads extends continuously across the screw shaft on a portion consisting of from the pinpoint surgical cutting tip at a first end of the shaft through the dynamic surgical region and through the stabilizing surgical region;
wherein the set of threads comprises a first set of minor diameters extending through the dynamic surgical region, the first set of minor diameters comprising four progressively increasing parallel minor diameters from the pinpoint surgical tip toward an interface of the dynamic surgical region with the stabilizing surgical region,
wherein the first set of minor diameters comprises:
a first minor diameter of 0.25 mm,
a second minor diameter of 0.43 mm,
a third minor diameter of 0.79 mm, and
a fourth minor diameter of 1.12 mm; and
wherein the set of threads on the stabilizing surgical region comprise a second set of minor diameters, the second set of minor diameters being of equal size extending from the interface of the dynamic surgical region with the stabilizing surgical region toward the first end of the annular region;
wherein the first set of minor diameters are parallel minor diameters;
wherein the adjustable, self-drilling, tenting screw terminates at one end at the pinpoint surgical tip;
wherein the adjustable, self-drilling, tenting screw is securable into maxillary or mandibular bone; and
wherein the first set of minor diameters enables the pinpoint surgical tip of the adjustable, self-drilling, tenting screw to function as its own osteotome;
wherein the adjustable, self-drilling tenting screw head comprises three regions comprising:
a first head region comprising a first taper extending from a top of the screw head to a second region;
the second head region having a diameter wider than a major diameter of any of the annulars and threads; and
a third head region comprising a second taper extending from the second region to an interface with the tapered region;
wherein only the stabilizing surgical region and the dynamic surgical region include helical threads;
wherein the adjustable, self-drilling, tenting screw is one-piece;
wherein the first set of minor diameters are parallel minor diameters;
wherein the second set of minor diameters are parallel minor diameters; and
wherein the tapered region is smooth.

2. The screw of claim 1, wherein the second set of minor diameters is 1.22 mm.

3. The screw of claim 1, wherein the screw is drivable into at least one of mandibular bone or maxillary bone.

4. An adjustable, self-drilling, tenting screw, consisting of:
a screw head comprising a screwdriver receptor site;
a tapered region that interfaces with the screw head,
wherein the tapered region has a first end and a second end,
wherein the first end comprises a minimum diameter of the tapered region,
wherein a minimum diameter of the tapered region interfaces with an annular of a plurality of annulars, wherein each annular of the plurality of annulars are parallel to one another,
wherein the second end comprises a maximum diameter of the tapered region, and wherein the second end interfaces with an underside of the screw head;
a shaft having a dynamic surgical region and a stabilizing surgical region, the shaft comprising a set of threads disposed thereon;
an annular region comprising the plurality of annulars, wherein each of the annulars of the plurality are separated by an annular concavity, and wherein each annular of the plurality has a diameter equal to a maximum major diameter of the set of threads;
wherein a first end of the annular region interfaces with the stabilizing surgical region;
wherein a second end of the annular region interfaces with the first end of the tapered region;
wherein the set of threads extends continuously across the screw shaft on a portion consisting of from the pinpoint surgical cutting tip at a first end of the shaft through the dynamic surgical region and through the stabilizing surgical region;
wherein the set of threads comprises a first set of minor diameters extending through the dynamic surgical region, the first set of minor diameters comprises four progressively increasing parallel minor diameters from the pinpoint surgical tip toward an interface of the dynamic surgical region with the stabilizing surgical region,
wherein the first set of minor diameters comprises:
a first minor diameter of 0.25 mm,
a second minor diameter of 0.43 mm,
a third minor diameter of 0.79 mm, and
a fourth minor diameter of 1.12 mm; and
wherein the set of threads on the stabilizing surgical region comprises a second set of minor diameters, the second set of minor diameters being of equal size extending from the interface of the dynamic surgical region with the stabilizing surgical region toward the first end of the annular region;
wherein the first set of minor diameters are parallel minor diameters;
wherein the adjustable, self-drilling, tenting screw terminates at one end at the pinpoint surgical tip;
wherein the adjustable, self-drilling tenting screw is securable into maxillary or mandibular bone; and
wherein the first set of minor diameters enables the pinpoint surgical tip of the adjustable, self-drilling, tenting screw to function as its own osteotome;
wherein the screw head comprises three regions comprising:
a first head region comprising a first taper extending from a top of the screw head to a second region;
the second head region having a diameter wider than a major diameter of any of the annulars and threads; and
a third head region comprising a second taper extending from the second region to an interface with the tapered region;
wherein only the stabilizing surgical region and the dynamic surgical region include helical threads;
wherein the adjustable, self-drilling, tenting screw is one-piece;
wherein the first set of minor diameters are parallel minor diameters;
wherein the second set of minor diameters are parallel minor diameters; and
wherein the tapered region is smooth.

5. The screw of claim 4, wherein the second set of minor diameters is 1.22 mm.

6. The screw of claim 4, wherein the screw is securable into at least one of mandibular bone or maxillary bone.

* * * * *